United States Patent
Andre et al.

(10) Patent No.: US 6,541,023 B1
(45) Date of Patent: Apr. 1, 2003

(54) USE OF COLLAGEN OF AQUATIC ORIGIN FOR THE PRODUCTION OF SUPPORTS FOR TISSUE ENGINEERING, AND SUPPORTS AND BIOMATERIALS OBTAINED

(75) Inventors: Valérie Andre, Ampuis (FR); Nabil Abdul Malak, Caluire (FR); Alain Huc, Ste. Foy les Lyons (FR)

(73) Assignee: Coletica, Lyons (FR)

( * ) Notice: Subject to any disclaimer, the term of this patent is extended or adjusted under 35 U.S.C. 154(b) by 0 days.

(21) Appl. No.: 09/616,282

(22) Filed: Jul. 14, 2000

(30) Foreign Application Priority Data

May 26, 2000 (FR) .............................. 00 06748

(51) Int. Cl.[7] .......................... A61F 2/10; A61K 38/39; C07K 14/78
(52) U.S. Cl. ...................... 424/422; 424/423; 424/424; 424/425; 424/443; 424/484; 435/397; 435/398; 435/401; 435/402; 530/356; 623/15.12
(58) Field of Search ................... 424/422, 423, 424/424, 425, 426, 443, 444, 484; 435/395, 397, 398, 401, 402; 527/200, 201, 202, 203, 204, 205, 206, 207; 530/356; 623/15.12

(56) References Cited

U.S. PATENT DOCUMENTS

| | | | |
|---|---|---|---|
| 5,093,474 A | 3/1992 | Grossman et al. | 530/355 |
| 5,116,824 A * | 5/1992 | Miyata et al. | 514/55 |
| 5,166,187 A | 11/1992 | Collombel et al. | 514/21 |
| 5,264,551 A | 11/1993 | Petite et al. | 530/356 |

(List continued on next page.)

FOREIGN PATENT DOCUMENTS

| | | |
|---|---|---|
| DE | 226 153 A3 | 8/1995 |
| EP | 0 602 297 A1 | 6/1994 |
| EP | 0 686 402 A1 | 12/1995 |
| EP | 0 753 313 A1 | 1/1997 |
| EP | 0 789 074 A1 | 8/1997 |
| EP | 842670 A1 * | 5/1998 |
| FR | 592603 A | 8/1925 |
| FR | 2 679 779 | 2/1993 |
| FR | 2 724 563 | 3/1996 |
| FR | 2 783 429 | 3/2000 |
| GB | 2 238 051 A | 5/1991 |
| WO | WO 89/08467 | 9/1989 |
| WO | WO 90/12055 | 10/1990 |
| WO | WO 91/16010 | 10/1991 |
| WO | WO 95/17428 | 6/1995 |
| WO | WO 96/08277 A1 | 3/1996 |
| WO | WO 97/20569 | 6/1997 |
| WO | WO 99/19005 A | 4/1999 |

OTHER PUBLICATIONS

Boyce et al. "Structure of a Collagen–GAC Dermal Skin Substitute Optimized for Cultured Human Epidermal Keratinocytes". *Journal of Biomedical Materials Research*, vol. 22, 939–957 (1988).

French Search Report dated Feb. 2, 2000.

Chemical Abstracts, vol. 112, No. 8. Skrodzki et al. "Manufacture of aqueous collagen–containing solutions from fish skin," Feb. 18, 1990. XP–002127982.

Josephson et al. "Bisulfite Suppression of Fish Aromas, "*Journal of Food Science*, vol. 48 (1983): pp. 1064–1067. XP002127981.

Patent abstracts of Japan, vol. 15, No. 275, JP 03–094633 (Ishiwatari), Apr. 19, 1991.

(List continued on next page.)

Primary Examiner—Jeffrey E. Russel
(74) Attorney, Agent, or Firm—Merchant & Gould P.C.

(57) ABSTRACT

Use of collagen of aquatic origin for the production of supports for tissue engineering is disclosed. The collagen may be obtained from fish skin, preferably in its native form. Novel tissue engineering supports with a low risk of contamination are produced.

91 Claims, 1 Drawing Sheet

U.S. PATENT DOCUMENTS

| | | | |
|---|---|---|---|
| 5,273,900 A | 12/1993 | Boyce | 435/240.23 |
| 5,331,092 A | 7/1994 | Huc et al. | 530/356 |
| 5,412,076 A | 5/1995 | Gagnieu | 530/356 |
| 5,420,248 A | 5/1995 | Devictor et al. | 530/356 |
| 5,714,582 A * | 2/1998 | Wolfinbarger | 530/356 |
| 6,271,350 B1 * | 8/2001 | Shimizu et al. | 530/356 |

OTHER PUBLICATIONS

Yeh et al. "A Novel Native Matrix for Tissue Engineering. Analysis of Cell–Matrix Interaction". Faseb Journal, vol. 14, No. 4, Mar. 15, 2000.

Derwent accession No. 1995–151478 & JP 07 075566 A, Marino Forum 21 SH, Mar. 20, 1995.

Wang et al. "Collagen Fibres with Improved Strength for the Repair of Soft Tissue Injuries". Biomaterials, vol. 15, No. 7 (1994): pp. 507–512.

Giraud–Guille et al. "Structural Aspects of Fish Skin Collagen which Forms Ordered Arrays via Liquid Crystalline States". Biomaterials, vol. 21, No. 9 (May 2000): pp. 899–906.

Co–pending application 09/435934 entitled: "Collagen Product Containing Collagen of Marine Origin with a Low Odor and Preferably with Improved Mechanical Properties, and its Use in the Form of Cosmetic or Pharmaceutical Compositions or Products", filed Nov. 9, 1999.

Co–pending application 09/616526 entitled: "Processes for the Preparation of Novel Collagen–Based Supports for Tissue Engineering, and Biomaterials Obtained", filed Jul. 14, 2000.

International Search Report dated Feb. 28, 2001.

International Search Report dated Mar. 16, 2001.

* cited by examiner

USE OF COLLAGEN OF AQUATIC ORIGIN FOR THE PRODUCTION OF SUPPORTS FOR TISSUE ENGINEERING, AND SUPPORTS AND BIOMATERIALS OBTAINED

SUBJECT OF THE INVENTION

The invention relates essentially to the use of collagen of aquatic origin for the production of supports for tissue engineering, and to such supports and biomaterials.

TECHNOLOGICAL BACKGROUND

Collagen is a particularly favorable substrate for cell development, which is why this protein is very widely used in several forms—matrices, gels or films—for the production of reconstructed tissues containing living cells.

In the field of tissue engineering, a technique which promises to have a great future, collagen has afforded the production of artificial skin or cartilage in particular. To achieve a satisfactory result, the collagen has to be protected from enzymatic degradation due to cell metabolism, either by physical or chemical crosslinking processes, or by the presence of natural macromolecules which interact strongly with the protein, or finally by a combination of both systems.

Hitherto, for these tissue engineering applications, the collagen used in supports for receiving cells was extracted from mammals and most frequently from bovine skin. The choice of this source was due to the good mechanical properties of the protein obtained after extraction, to its resistance to enzymatic degradation and finally to its amino acid composition, which is very similar to that of human collagen. For all these reasons, it was legitimate to think that this collagen was the only one suitable for the culture of human cells.

PURPOSES OF THE INVENTION

Now, the inventors have noticed, unexpectedly, that human cells develop very well on or inside certain supports consisting of preferably crosslinked fish collagen. In addition, the inventors have been able to demonstrate that human cells cultivated in these biomaterials preserve a normal metabolism. These biomaterials can be either films, or compressed sponges, or porous matrices, which will be described together with their methods of preparation in the Examples given below.

One object of the present invention is to solve the new technical problem which consists in providing novel supports for tissue engineering suitable for forming novel biomaterials, i.e. suitable for allowing a good proliferation of the normal, genetically modified or malignant living cells to be cultivated on said support and to be used within the framework of these novel biomaterials, containing said living cells, for subsequent proliferation in vitro or in vivo.

A further object of the present invention is to solve the new technical problem which consists in providing novel supports for tissue engineering at a low manufacturing cost and also with a low risk of contamination, thus making them particularly suitable for the provision of novel biomaterials.

A further main object of the present invention is to solve the new technical problem which consists in providing novel supports for tissue engineering which are particularly suitable for allowing the multiplication of normal, genetically modified or malignant living cells, in vitro or in vivo, and whose structure is sufficiently compatible with in vivo use in a mammal, particularly an animal or, preferably, a human being, while at the same time being different from the constitution of the tissues of said mammal, such as an animal or, preferably, a human being, so as to allow subsequent differentiation between the newly synthesized tissues and the old tissues of said mammal, preferably a human being.

The present invention solves all these technical problems for the first time in a satisfactory manner, at low cost, with a low risk of contamination or without contamination, while at the same time easily making it possible to identify the newly synthesized tissues, which is particularly non-obvious and unexpected for those skilled in the art.

SUMMARY OF THE INVENTION

Thus, according to a first feature, the present invention relates to the use of collagen of aquatic origin for the production of supports for tissue engineering, as well as the corresponding method of production thereof.

The expression "collagen of aquatic origin" is understood as meaning a collagen derived from collagen-containing tissues of living beings of aquatic origin; these living beings are well known to those skilled in the art and include for example, without implying a limitation, aquatic mammals, particularly marine mammals, jellyfish and saltwater or freshwater fish. Furthermore, those skilled in the art know that the skin of these living beings contains essentially collagen.

In one advantageous embodiment, the collagen is obtained from fish skin, preferably in its native form.

In another advantageous embodiment of the invention, the mechanical strength of the collagen or its resistance to enzymatic digestion is increased either by chemical and/or physical crosslinking, or by the addition of a natural macromolecule which interacts strongly with collagen, or by a combination of both processes.

In yet another advantageous embodiment of the invention, the collagen is used in the form of a porous matrix prepared from a collagen gel which has preferably undergone a lyophilization step.

In yet another advantageous variant, the above-mentioned porous matrix is crosslinked by a physical method, preferably by thermal dehydration, or TDH.

In yet another advantageous variant, the above-mentioned porous matrix is crosslinked by a chemical method, preferably with diphenylphosphorylazide, or DPPA, or with a carbodiimide and/or N-hydroxysuccinimide, or with glutaraldehyde.

In one advantageous embodiment, the above-mentioned collagen can take the form of a porous matrix prepared from marine collagen (preferably native) mixed with chitosan and optionally at least one glycosaminoglycan, preferably chondroitin sulfate.

In yet another advantageous embodiment of the invention, the above-mentioned collagen can take the form of a porous matrix prepared from a collagen gel, said porous matrix being covered on at least one side with an essentially compact collagen membrane consisting either of a collagen film prepared by drying a collagen gel, preferably in air or a gaseous fluid, or of a very highly compressed collagen sponge.

In another advantageous variant, the above-mentioned compression of the very highly compressed collagen sponge is carried out at a pressure of at least about 50 bar (about $50.10^5$ Pascal (Pa)) and preferably of between 50 bar ($50.10^5$ Pa) and 200 bar ($200.10^5$ Pa), this compression optionally having been carried out at a temperature of between 20° C. and 80° C. and preferably of between 40° C. and 60° C.

According to yet another advantageous characteristic of the invention, at least one of the two layers, i.e. the porous layer and the essentially compact membrane, comprises normal, genetically modified or malignant living cells originating particularly from young or elderly subjects.

In one advantageous embodiment, the living cells are selected from the group consisting of fibroblasts, keratinocytes, melanocytes, Langerhans' cells originating from the blood, endothelial cells originating from the blood, blood cells, particularly macrophages or lymphocytes, adipocytes, sebocytes, chondrocytes, osteocytes, osteoblasts and Merkel's cells originating from the blood, said cells being normal, genetically modified or malignant.

In one particularly advantageous embodiment, the porous layer contains normal, genetically modified or malignant fibroblasts and the essentially compact membrane contains normal, genetically modified or malignant living cells selected particularly from keratinocytes, melanocytes, Merkel's cells originating from the blood, Langerhans' cells originating from the blood, sebocytes, cells originating from the blood, and nerve cells.

In yet another advantageous embodiment of the invention, it may be of particular value to prepare either "young" reconstructed skin using cells taken from young subjects, or "aged" reconstructed skin obtained from cells taken from elderly subjects. These models will enable us to improve our knowledge of the skin ageing process and study the influence of active agents on this process.

In another particularly advantageous embodiment, the above-mentioned essentially compact membrane is prepared prior to combination with the porous layer, preferably comprising a collagen sponge, particularly by preparing the membrane and depositing it on a collagen gel before the whole is frozen and lyophilized.

According to a second feature, the present invention also covers a support for tissue engineering which comprises collagen of aquatic origin as defined above or as resulting from the following description taken in its entirety and including the Examples, which form an integral part of the present invention in their generality, and as regards any characteristic which appears to be novel by comparison with any state of the art, this characteristic being taken in its function and in its generality, independently of the context of the Example.

According to a third feature, the present invention also covers a biomaterial, for example in the form of a reconstituted connective tissue or reconstituted skin, which has been prepared from the collagen of aquatic origin as defined above in all these features and also as resulting from the following description, as for the support of the second feature above.

within the framework of the present description and the claims, the expression "supports for tissue engineering" denotes supports to be used for carrying out the culture and proliferation of normal, genetically modified or malignant living cells, whether in vitro or in vivo, this proliferation preferably being applied in vivo to a mammal, comprising an animal and, preferably, a human being. It is understood that the invention has a particularly preferred use within the framework of tissue engineering for the manufacture of biomaterials, for example in the form of reconstituted connective tissues or reconstituted skin. within this framework, a first step will generally be the culture of the support with said living cells in vitro to give a biomaterial, for example in the form of a reconstituted connective tissue or reconstituted skin, and then a second step will be the use of this biomaterial as reconstituted connective tissue or reconstituted skin in vivo on a mammal, for example an animal or, preferably, a human being, in order to reconstitute a connective tissue damaged or removed by surgery or, likewise, in order to reconstitute skin to replace an area damaged or removed by surgery for whatever medical reason.

Advantageously, the support for tissue engineering or, preferably, the biomaterial, for example in the form of a reconstituted connective tissue or reconstituted skin, comprises cells obtained either substantially exclusively from young subjects or substantially exclusively from elderly subjects, in particular for studying the tissue ageing process, and especially the skin ageing process, and optionally for testing the efficacy of active ingredients or principles on this process.

The invention further relates to an artificial skin which is essentially prepared from substantially exclusively young cells originated from young subjects.

The invention further relates to an artificial skin which is essentially prepared from substantially exclusively aged cells originated from elderly subjects.

The invention further relates to an artificial skin comprising living cells essentially prepared from substantially exclusively young cells originated from young subjects.

The invention further relates to an artificial skin comprising living cells essentially prepared from substantially exclusively aged cells originated from elderly subjects.

According to a further aspect, the invention relates to an artificial skin comprising a support comprising or substantially exclusively constituted from marine collagen, preferably fish collagen.

The invention further relates to a method of in vitro testing of the efficacy of a potential active substance comprising using an artificial skin comprising living cells essentially prepared substantially exclusively from young cells taken from young subjects, in combination with a support comprising or essentially consisting of marine collagen.

The invention further relates to a method of in vitro testing of the efficacy of a potential active substance comprising using an artificial skin comprising living cells essentially prepared substantially exclusively from aged cells taken from elderly subjects, in combination with a support comprising or essentially consisting of marine collagen.

The invention further relates to a method of reconstructing damaged areas of skin in vivo comprising performing said reconstruction with an artificial skin comprising living cells, and prepared essentially from a support comprising or essentially consisting of marine collagen, preferably fish collagen.

In each and all of the above features, aspects or embodiments of the invention, it is advantageous that at least one of the porous matrix or layer, and of the essentially compact membrane is produced from a collagen gel containing a mixture of soluble collagen and insoluble collagen. Preferably, said insoluble collagen is comprising or is substantially essentially consisting of collagen fibers.

According to another advantageous feature, at least a part of, or substantially all of, the collagen is selected from the group consisting of type I collagen and type III collagen, said feature being of course combinable with any other feature of the present invention.

Thus it is seen that the invention provides a general solution to the above-mentioned new technical problems in a particularly simple manner, at low cost, with a low risk of contamination and with a capacity to differentiate between aquatic collagen and mammalian collagen or, preferably, human collagen, newly synthesized in the course of in vivo use.

In fact, the use of fish collagen in the production of living artificial tissues has three essential advantages compared with the mammalian source:

The fish skin generally used as the raw material can be obtained in abundance under very clean conditions.

The danger of infectious contamination is very low. In particular, there is no known risk of transmitting agents of the prion type.

Finally, as the amino acid composition of fish collagen is relatively dissimilar to that of human collagen, the two proteins can be differentiated relatively easily by means of specific antibodies. This methodology will be very valuable particularly in "in vitro" tests or in "in vivo" healing studies.

Moreover, the use of marine collagen will make immunolabeling very effective and allow differentiation between marine collagen and newly synthesized collagen.

Fish collagen has a native structure which protects it from enzymatic degradation due to proteases and which is largely responsible for its mechanical properties. It will therefore be very important that the treatments used during the extraction and purification operations degrade the protein structure as little as possible. This means that the helical structure and the intermolecular and intramolecular crosslinks should be preserved as far as possible. The inventors achieved this more particularly by implementing the process described in patent U.S. Pat. No. 5,331,092 granted on Jul. 19, 1994. Nevertheless, for particular applications, it may be possible to envisage the use of partially decrosslinked collagen, for example atelocollagen, i.e. collagen which has lost part of its telopeptides.

Then, for the majority of tissue engineering applications, the mechanical properties of the collagen will be enhanced and its resistance to enzymatic digestion increased either by chemical and/or physical crosslinking techniques, or by the addition of natural macromolecules which interact strongly with the protein, or finally by a combination of both processes.

The protection of fish collagen will be all the more important because its natural stability is lower than that of mammalian collagen, the latter characteristic being due to a lower hydroxyproline content.

The biomaterials described above may be inoculated with living cells to create living artificial tissues which may be used either in the field of "in vitro" tests or in the pharmaceutical field for repairing injured tissues.

BRIEF DESCRIPTION OF EXAMPLES AND DRAWINGS

Other objects, characteristics and advantages of the invention will become clearly apparent from the following explanatory description referring to Examples of the preparation of forms of collagen of aquatic origin which can be used within the framework of the invention for the production of supports for tissue engineering, and thus constituting such supports as well as biomaterials, which are given simply by way of illustration and cannot therefore in any way limit the scope of the invention.

In the Examples, the temperature is given in degrees Celsius, the pressure is atmospheric pressure and the percentages are given by weight, unless indicated otherwise.

Examples 1 to 13 are of course Examples of the preparation of collagen which can be used as a tissue engineering support according to the invention.

Examples 14 to 16 are notably comparative tests within the framework of the use of this collagen of aquatic origin, in the forms prepared in some of Examples 1 to 13, within the framework of the production of supports for tissue engineering.

DETAILED DESCRIPTION OF THE INVENTION INVOLVING BEST MODE

EXAMPLE 1

Figure 1:
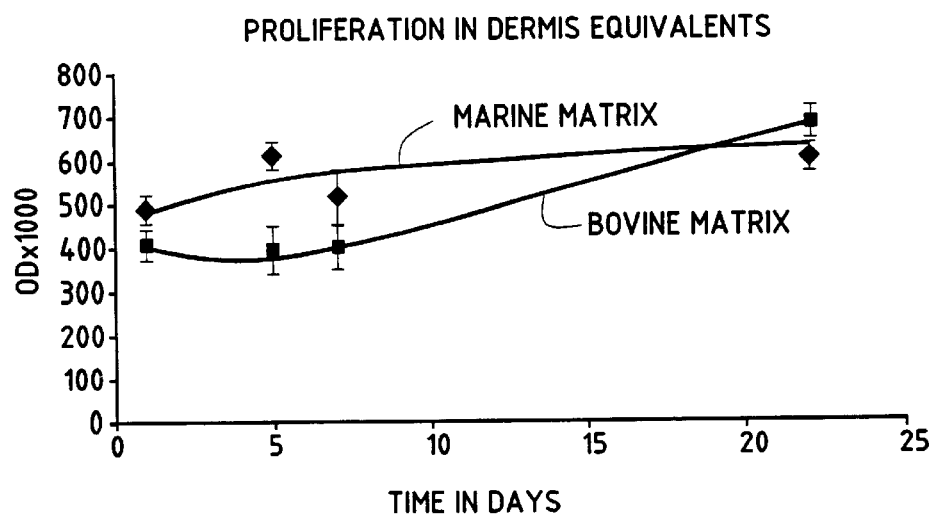
FIG. 1 shows the proliferation of normal human fibroblasts in dermis equivalents, the time expressed in days being plotted on the abscissa and the optical density×1000 being plotted on the ordinate and increasing in units of 100; the curve with diamonds is the one obtained when the support used is a porous matrix of aquatic collagen, in this case fish collagen, and the curve with squares is the one obtained with bovine collagen.

Preparation of a Porous Matrix of Aquatic Native Collagen

The collagen is obtained by the technique of patent U.S. Pat. No. 5,331,092 granted on Jul. 19, 1994.

A—Preparation of the Aquatic Native Collagen

A collagen gel is prepared from ventral sole skin which is ground and then washed with a phosphate buffer of pH 7.8 having the following composition: 0.78 g/l of potassium dihydrogenphosphate and 21.7 g/l of disodium monohydrogenphosphate. The washing is carried out with agitation for one hour at a rate of 5 l of buffer per kg of ground material. The phosphate is then removed by means of two successive washes with softened water, followed by continuous centrifugation at 4000 rpm (Rousselet centrifuge), at a rate of 5 l of water per kg of ground material. The ground material is then acidified with 0.25 M acetic acid solution at a rate of 1 kg of ground material to 10 l of solution. The gel is then centrifuged at 4000 rpm for 5 min.

The gel to be used consists of the supernatant obtained, which has a collagen concentration of between 0.5 and 2%.

B—Preparation of the Porous Matrix from the Collagen Gel Obtained Above

This gel is poured into a lyophilization tray at a rate of 20 g/cm². It is then lyophilized after freezing at −30° C. and heating at +32° C. The total lyophilization time is 16 hours under a pressure of 400 microbar. The matrix obtained is then crosslinked by thermal dehydration (TDH), which consists in heating in an oven at 110° C. under a vacuum of 400 microbar for 16 hours.

EXAMPLE 2

Preparation of a Porous Matrix Crosslinked with Diphenylphosphorylazide (DPPA) by the Technique Described in European Patent No. 466 829 of Jul. 24, 1996

The collagen matrix of Example 1 is incubated for 24 h in a solution containing 5 to 250 µl DPPA/g collagen in 100 ml of dimethylformamide (DMF). The collagen is then rinsed in 100 ml of DMF to remove the DPPA. The DMF is then removed by rinsing in 100 ml of a borate buffer solution of pH 8.9 (0.04 M sodium tetraborate, 0.04 M boric acid).

The collagen is finally incubated overnight in the same borate buffer, the borate buffer then being removed by continuous rinsing with softened water for 6 h.

EXAMPLE 3
Preparation of a Porous Matrix Crosslinked with Carbodimide and N-hydroxy-succinimide The aquatic collagen matrix of Example 1 is crosslinked with EDC (ethyl-dimethylaminopropylcarbodiimide) at a concentration of 0.23 to 0.69 g/g collagen and with NHS (N-hydroxysuccinimide) at a concentration of 0.42 g/g collagen.

After rinsing with softened water, the collagen is lyophilized again.

EXAMPLE 4
Preparation of a Porous Matrix Crosslinked with Glutaraldehyde

The porous matrix of aquatic collagen of Example 1 is crosslinked for 24 to 96 h in a solution containing 0.6 to 1% of GTA at 20° C.

After rinsing with softened water, the collagen is lyophilized again.

EXAMPLE 5
Porous Matrix Prepared with the Aquatic Native Collagen of Example 1 in Association with Chitosan and a Glycosaminoglycan as Described in European Patent No. 296078 of May 29, 1991

A solution of 2.5 g of chitosan in 356 ml of water and 1.9 ml of acetic acid, and then a solution containing 1 g of chondroitin 4-sulfate in 400 ml of softened water, are added to 600 g of 1.5% collagen gel. The mixture, which has a pH of about 4.0, is subsequently agitated and then lyophilized.

The sponge obtained is crosslinked by TDH.

EXAMPLE 6
Porous Matrix Described in Example 1, Covered with a Collagen Film A—Preparation of the Film The collagen gel, which has a solids content of between 0.3 and 0.8%, is dried in an oven at 30° C. or under a hood at a rate of 0.5 g gell/cm² tray. 10 to 40% of glycerol can be added to the collagen gel. The collagen dried under these conditions forms a transparent film.

B—Association of the Film with the Porous Matrix Described Above

The aquatic native collagen gel with a solids content of 0.5% to 2% is deposited in a lyophilization tray at a rate of 0.5 g per cm², the collagen film is then deposited on this gel and the whole is lyophilized. The lyophilizate obtained is crosslinked by TDH.

EXAMPLE 7
Porous Matrix Prepared with an Acid-soluble Collagen Gel and Covered with a Collagen Film The process is that indicated in Example 6, the only difference being in the nature of the gel poured onto the film, which consists of acid-soluble collagen prepared by a technique well known to those skilled in the art.

EXAMPLE 8
Porous Matrix Prepared with an Atelocollagen Gel and Covered with a Collagen Film The process is that indicated in Example 6, the only difference being in the nature of the gel poured onto the film, which consists of atelocollagen, i.e. telopeptide-free collagen prepared by a technique well known to those skilled in the art.

EXAMPLE 9
Porous Matrix Consisting of Collagen Associated with Chitosan and a Glycosaminoglycan and Covered with a Collagen Film The process is that indicated in Example 6 except that in this case the gel poured onto the collagen film consists of collagen, chitosan and a glycosaminoglycan. aminoglycan. The preparation of this gel is described in Example 5.

EXAMPLE 10
All the porous matrices described above, covered with a collagen film, can be crosslinked by the techniques described in Examples 2, 3 and 4.

EXAMPLE 11
Porous Matrix of Collagen Only Described in Example 1 Covered with a Compressed Collagen Sponge A—Preparation of the Compressed Sponge The collagen gel prepared as in Example 1, with a solids content of between 0.3 and 1.5%, is lyophilized to give a sponge weighing between 0.5 and 2 g/cm².

The lyophilizate is compressed for 5 to 60 seconds at a temperature of between 20 and 60° C. and a pressure of between 50 and 200 bar (50 to $200.10^5$ Pa).

B—Association of the Compressed Sponge with the Porous Matrix

The collagen gel described in Example 1 is deposited in a lyophilization tray at a rate of 0.5 g per cm². The compressed sponge is then deposited on this gel and the whole is lyophilized to give a porous collagen sponge covered with a compressed collagen sponge. The whole is crosslinked by TDH as described in Example 1.

EXAMPLE 12
Porous Matrix Consisting of Collagen, Chitosan and Glycosaminoslcan, as Described in Example 5. Covered with Compressed Sponge The collagen, chitosan and glycosaminoglycan gel prepared by the process of Example 5 is deposited in a lyophilization tray at a rate of 0.5 g per cm², the compressed sponge is then deposited on this gel and the whole is lyophilized. The lyophilizate is then crosslinked by TDH as described in Example 1.

EXAMPLE 13
All the porous matrices described above, covered with a compressed collagen sponge, can be crosslinked by the techniques described in Examples 2, 3 and 4.

EXAMPLES 14 TO 16
Tests for Comparing the Cell Metabolism of Bovine and Aquatic Collagen Matrices

EXAMPLE 14
Test for Cell Viability of Fibroblasts

I—Preparation of the Dermis Equivalents

For this comparative test, a DPPA-crosslinked aquatic porous matrix according to Example 2 is prepared first.

By way of comparison, a comparative porous matrix called a bovine matrix, also crosslinked with DPPA, is prepared with collagen of bovine origin under the same conditions as those of Example 2.

Normal human fibroblasts, taken from a young donor pool used at the 7th passage, are inoculated into each of the aquatic and bovine matrices at a rate of 250,000 cells per cm in the case of the proliferation and protein synthesis study, and at a rate of 300,000 cells per $cm^2$ in the case of the aquatic and bovine matrices intended for the histological studies.

These aquatic and bovine matrices are cultured in a medium composed of DMEM/HAM F12 in a ratio of 50/50 (v/v) supplemented with 10% of fetal calf serum, 100 IU/ml of penicillin, 25 µg/ml of gentamycin, 1 µg/ml of amphotericin B and 50 µg/ml of vitamin C.

This culture is carried out for 1 month, the culture medium being changed 3 times a week.

II—Analyses Performed

1) Measurement of Cell Viability by Reaction with MTT

1% by weight of MTT (i.e. 3-(4-(dimethylthiazol-2-yl)-2,5-diphenyl-tetrazolium bromide) is added to the culture medium.

Incubation is carried out for 2.5 hours at 37° C.

After this incubation period, the conversion product (formazan blue) is solubilized in DMSO and its optical density is read at 550 nm.

The optical density obtained is proportional to the activity of the succinate dehydrogenases, which are capable of converting the bright yellow tetrazolium salt, MTT, to blue crystals of formazan.

The cell viability was measured after 1, 5, 7 and 22 days and one month of culture.

To determine the mean values, 6 samples were prepared for each matrix.

TABLE I

RESULTS

| Days | Aquatic matrix | Mean standard deviation | Bovine matrix | Mean standard deviation |
|---|---|---|---|---|
| 1 | 487 | 24 | 403 | 40 |
| 5 | 604 | 19 | 393 | 59 |
| 7 | 520 | 56 | 398 | 64 |
| 22 | 608 | 30 | 680 | 40 |

These results are also used for the curves in the attached FIG. 1.

It will be noted that the curve with the diamonds is that obtained with the aquatic matrix and the curve with the squares is that obtained with the bovine matrix.

The results show, totally surprisingly, that the aquatic matrix constitutes a support which allows not only the survival of normal human fibroblasts but also the proliferation of these normal human fibroblasts, while at the same time even constituting a much better culture support during the first three weeks.

It can therefore be concluded from these tests that, surprisingly, aquatic collagen is particularly suitable for the production of a tissue engineering support, in particular for applications in vitro and even, above all, in vivo for forming biomaterials containing living cells, particularly and preferably those of human beings.

2) Measurement of Protein Synthesis

The synthesis of proteins secreted over 3 days in a culture medium free of fetal calf serum was evaluated after one month of maturation of the dermis equivalents as obtained after one month of culture under the conditions reported above in the preparation of the dermis equivalents.

The assay is performed by the microBCA method of Pierce.

The cell density was evaluated in parallel by an MTT test under the conditions described above.

The relative protein content corresponds to the protein content per unit of cell density expressed as the optical density, or OD, so that the cell concentration in question is equivalent. The results obtained are shown in Table II below:

TABLE II

RESULTS OF PROTEIN SYNTHESIS

|  | Aquatic matrix | | Bovine matrix | |
|---|---|---|---|---|
| Collagen of the support | Mean | * | Mean | * |
| Cell density (OD) | 2.12 | 0.09 | 1.91 | 0.13 |
| Proteins (µg/ml) | 494 | 48 | 499 | 32 |
| Relative protein content | 233 | 18 | 262 | 23 |

*: Mean standard deviation

As in Table I, the mean is based on 6 samples.

3) Histology

The dermis equivalents obtained after culture of the aquatic and bovine collagen matrices for 21 days are fixed in 2% paraformaldehyde solution and then post-fixed in osmium tetroxide solution, dehydrated, included in Epon, sectioned and observed by transmission electron microscopy (Jeol 1200) at CMEAGB (Lyon, France).

Conclusions

These results indicate a very good colonization of the three-dimensional matrices, whether they be aquatic or bovine. After three weeks of culture, the cell density is equivalent in both types of matrices. However, the aquatic matrix seems to allow a better cell adhesion at the beginning of the experiment, as indicated by the proliferation study in the first week of culture, and hence a better colonization for short culture times.

As far as the protein syntheses are concerned, the fibroblast synthesis capacities (relative protein contents) are also equivalent after one month of culture.

These results indicate that the aquatic collagen matrices developed made it possible to prepare dermis equivalents of good quality, the results obtained with these matrices being comparable to those obtained with bovine collagen matrices.

In transmission electron microscopy, fibroblasts could be observed in the matrices of bovine and aquatic origin. In both types of matrix, the presence of a copious neosynthesized extracellular matrix is noted. The neosynthesized extra-cellular matrix can be differentiated by virtue of the periodic striation of the fibers of deposited collagen, compared with the collagen clusters forming the three-dimensional matrix of the initial sponge.

EXAMPLE 15

Influence of the Different Types of Crosslinking of the Aquatic Collagen Matrices on the Cell Viability The following tests are carried out in order to study the influence of the different types of crosslinking of the aquatic collagen matrices on the cell viability:

I) Preparation of the Dermis Equivalents a) Support or Matrix Used

Various collagen supports or matrices are prepared using different proportions of collagen in the collagen gel for producing the porous layer or matrix, and optionally using a different crosslinking agent, as follows:

1) Test 1

For this test, a porous matrix in the form of a porous sponge is produced from an aquatic collagen gel prepared from 1.3% by weight of aquatic collagen, which is frozen at −80° C., subjected to standard lyophilization according to Example 2 and then crosslinked with DPPA in a proportion of 250 μl per g of sponge in the dry state.

2) Test 2

For this test, a porous support in the form of an aquatic sponge is prepared from an aquatic collagen gel comprising The intensity of the fluorescence obtained is proportional to the metabolic activity of the cells.

The cell viability is measured on 10 samples after 1, 4, 6, 11 and 17 days of culture.

The results are expressed in Table III below.

The results are indicated in international units of fluorescence as a function of time.

TABLE III

| Time | CELL VIABILITY (IU of fluorescence) | | | | | | | |
|---|---|---|---|---|---|---|---|---|
| | TEST 1 | | TEST 2 | | TEST 3 | | TEST 4 | |
| (days) | Mean | SD* | Mean | SD* | Mean | SD* | Mean | SD* |
| 1 | 21,734 | 1184 | 30,535 | 1888 | 25,528 | 6820 | 28,461 | 3805 |
| 4 | 31,611 | 920 | 35,623 | 3544 | 36,404 | 3570 | 45,126 | 2930 |
| 6 | 43,144 | 2500 | 35,244 | 2095 | 37,819 | 4170 | 41,254 | 3396 |
| 11 | 42,808 | 1481 | 38,532 | 2537 | 42,442 | 3112 | 44,508 | 2329 |
| 17 | 45,484 | 2426 | 45,094 | 1470 | 43,963 | 8285 | 43,939 | 4521 |
| Order | 1 | | 2 | | 3 | | 4 | |

*Standard deviation 0.7% by weight of aquatic collagen, which is frozen at −80° C. and then subjected to standard lyophilization and crosslinked with DPPA in a proportion of 250 μl per g of dry sponge as in test 1.

3) Test 3

For this test, the procedure is as in Test 1 except that the crosslinking is carried out with EDC, according to Example 2, in a proportion of 0.46 g per g of dry sponge.

4) Test 4

A porous support is prepared which comprises a sponge of aquatic collagen obtained from an aquatic collagen gel comprising 1.1% by weight of aquatic collagen, which is frozen at −80° C. and then subjected to standard lyophilization and crosslinked with DPPA in a proportion of 250 μl per g of dry sponge as in Test 2, the difference being in the proportion of 1.1% by weight of aquatic collagen.

In all these tests, the aquatic collagen originates from ventral sole skin as in Example 2.

b) Culture of Fibroblasts on These Matrices

Normal human fibroblasts are used as in Example 14, but these are taken at the 8th passage.

Inoculation is carried out at a rate of 275,000 cells per cm².

The culture medium is composed of DMEM/HAM F12 50/50 (v/v) supplemented with 10% by weight of fetal calf serum, 100 IU/ml of penicillin, 25 μg/ml of gentamycin, 1 μg/ml of amphotericin B and 50 μg/ml of vitamin C.

Culture is carried out for 1 month, the medium being changed 3 times a week.

4 matrices are used for each test so as to take a mean for each type of test and measure the mean standard deviation.

II) Analyses Performed

Measurement of the Cell Viability by Reaction with Alamar Blue (Redox Marker)

Alamar blue is added at a rate of 2% by weight of the culture medium used, at the moment when it is desired to measure the cell viability on a sample taken from the culture medium.

After incubation for 2 h 20 min at 37° C., the fluorescence is read on the basis of an excitation at 530 nm and an emission at 590 nm.

Figure 2:
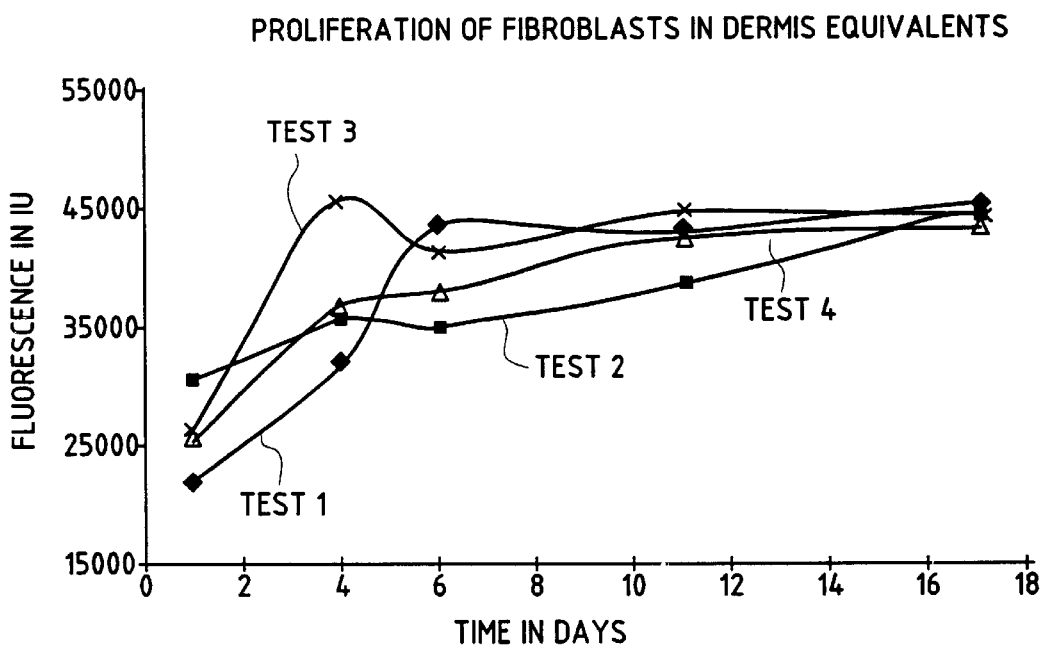
FIG. 2 shows a similar curve for the proliferation of fibroblasts in dermis equivalents, the time expressed in days being plotted on the abscissa and the fluorescence expressed in international units being plotted on the ordinate, starting at 15,000 and increasing in units of 10,000; the curve with solid diamonds represents the fluorescence obtained in test 1, the curve with squares represents that obtained in test 2, the curve with open triangles represents that obtained in test 3 and, finally, the curve with crosses represents that obtained in test 4.

The results in Table 3 are also used in the attached FIG. 2.

They show the curves of fibroblast proliferation in dermis equivalents.

The curve with solid diamonds corresponds to Test 1, the curve with solid squares corresponds to Test 2, the curve with triangles corresponds to Test 3 and the curve with crosses corresponds to Test 4.

The time is expressed in days on the abscissa and the fluorescence is expressed in IU with a scale starting at 15,000 and increasing to 55,000 in units of 10,000.

The results allow the following conclusions to be drawn.

Conclusions

The results indicate that the different matrices prepared can permit a good growth of fibroblasts after 17 days of culture. Irrespective of the preparation of the aquatic collagen matrices, the fibroblasts adhere well to their three-dimensional support and divide very rapidly to colonize the matrix.

The proliferation profile varies very slightly from one type of matrix to the other, but the fibroblast density is comparable after 17 days of culture, irrespective of the preparative process.

The different types of crosslinking employed, carried out either with DPPA or with EDC, do not seem to influence the cell renewal. After practically 3 weeks of culture, the stability of the matrices is excellent, there being little digestion and little contraction.

EXAMPLE 16

Test Demonstrating the Advantages of Aquatic Collagen for the Identification and Assay of Neosynthesized Human Collagen This test is similar to that of Example 14 except that histology is carried out with immunolabeling.

The test is performed as follows:

1) Preparation of the Dermis Equivalents

These are the dermis equivalents of Example 14, culture being carried out under the conditions of Example 14.

This culture is therefore carried out for three weeks with the medium being changed three times a week, the normal human fibroblasts having been inoculated at a rate of 300,000 cells per cm², as indicated in Example 14.

2) Histology a) Conventional Histology

Fixing is effected with paraformaldehyde at a concentration of 4% by weight, after which the material is dehydrated and included in paraffin.

This is followed by the preparation of 7 μm sections and Mallory Haidenhain staining after removal of the paraffin and rehydration.

b) Immunolabeling

Fixing is again effected with 4% by weight of paraformaldehyde, the material is included in Tissue Tek OCT compound, i.e. an inclusion liquid supplied by Miles, Elkhart, Ind., USA, and a 7 μm section is prepared in the cold.

Immunolabeling is performed with the following: i. a first rabbit anti-human type I collagen antibody (dilution 1/40), and ii. a second anti-rabbit antibody coupled with FITC (Fluorescein IsoThioCyanate) (dilution 1/160). DAPI (4',6-diamidino-2-phenylindole dilactate) is used as a counterstain.

3) Results

It is found that supports consisting of an aquatic matrix and a bovine matrix form more or less loose pores to which the fibroblasts adhere.

A greater proportion of fibroblasts is observed on the surface, forming a favorable covering over the dermis equivalent for the production of reconstructed skin. The distribution of the fibroblasts is homogeneous in aquatic and bovine sponges.

In immunolabeling, it is found that the matrix formed of bovine collagen is labeled by the anti-human type I collagen antibody (crossing).

On the other hand, the matrix of aquatic origin is only very weakly labeled by the anti-human collagen antibody.

The use of sponges composed of aquatic collagen therefore favors identification of the neosynthesized extracellular matrix.

These results are explained by Professor Hartmann's studies on the reactions of different antigens to different antibodies, determined by the optical density measurements after immunolabeling which are given below in Table IV, or Hartmann's table:

TABLE IV

Cross reaction with human, bovine and fish collagen (Elisa)

| Antigen | Sole type I collagen | Human type I collagen | Bovine I type collagen |
|---|---|---|---|
| Antibody | | | |
| 20111 (225) | | | |
| 1/25 | 190 | > | 815 |
| 1/50 | 210 | > | 548 |
| 1/100 | 73 | 1233 | 234 |
| 1/200 | 43 | 605 | 136 |
| 1/400 | 56 | 326 | 165 |
| 50121 (03) | | | |
| 1/25 | 180 | 1550 | > |
| 1/50 | 130 | 1094 | > |
| 1/100 | 158 | 536 | > |
| 1/200 | 96 | 305 | 967 |
| 1/400 | 109 | 215 | 728 |

TABLE IV-continued

Cross reaction with human, bovine and fish collagen (Elisa)

| Antigen | Sole type I collagen | Human type I collagen | Bovine I type collagen |
|---|---|---|---|
| 50171 (01) | | | |
| 1/25 | 1880 | 64 | 73 |
| 1/50 | 1043 | 193 | 32 |
| 1/100 | 571 | 51 | 33 |
| 1/200 | 523 | 51 | 87 |

(>: optical density greater than 2000)

The results are expressed in OD × $10^3$ (optical density at λ = 450 nm).

Key:
20111 (225): anti-human type I collagen
50121 (03): anti-bovine type I collagen
50171 (01): anti-fish (sole) type I collagen This Table of results shows that, irrespective of the antibody (anti-human type I collagen, anti-bovine type I collagen, anti-sole type I collagen) in immuno-labeling, the difference between human collagen and sole collagen is much greater than between human collagen and bovine collagen. Consequently, in a fish collagen matrix, the collagen synthesized by human fibroblasts may be identified much more easily. This confirms the results described above which were obtained by immunolabeling collagen synthesized in the fish collagen matrix with the anti-human type I collagen antibody, constituting a particularly unexpected and advantageous result of the invention.

What is claimed is:

1. A support for tissue engineering comprising:
a porous matrix prepared from a collagen gel of aquatic origin; and
a collagen membrane comprising a compressed collagen sponge, wherein said compression is carried out at a pressure of at least about 50 bar,
wherein said porous matrix is covered on at least one side with said collagen membrane.

2. The support of claim 1, wherein said collagen gel of aquatic origin is obtained from fish skin.

3. The support of claim 1, wherein said collagen gel of aquatic origin is obtained from fish skin in its native form.

4. The support of claim 1, wherein said porous matrix is prepared from aquatic collagen gel which has undergone a lyophilization step, and wherein said porous matrix has its mechanical strength or its resistance to enzymatic digestion increased by a physical crosslinking.

5. The support of claim 4, wherein said physical crosslinking comprises thermal dehydration.

6. The support of claim 1, wherein said porous matrix is crosslinked by a chemical method selected from the group consisting of: a treatment with diphenylphosphorylazide, a treatment with a carbodiimide, a treatment with N-hydroxysuccinimide, a treatment with glutaraldehyde, and combinations thereof.

7. The support of claim 1, wherein said collagen gel of aquatic origin is mixed with chitosan prior to formation of said porous matrix.

8. The support of claim 7, wherein said collagen gel of aquatic origin is mixed with at least one glycosaminoglycan prior to formation of said porous matrix.

9. The support of claim 8, wherein said glycosaminoglycan is chondroitin sulfate.

10. The support of claim 1, wherein said collagen membrane is of aquatic origin.

11. The support of claim 1, wherein at least one of said porous matrix and of said collagen membrane comprises living cells selected from the group consisting of normal living cells, genetically modified living cells and malignant living cells.

12. The support of claim 11, wherein said living cells originate from young subjects.

13. The support of claim 11, wherein said living cells originate from elderly subjects.

14. The support of claim 11, wherein said living cells originate from human subjects.

15. The support of claim 11, wherein said living cells are selected from the group consisting of fibroblasts, keratinocytes, melanocytes, Langerhans' cells originating from the blood, endothelial cells originating from the blood, Merkel's cells, blood cells, adipocytes, sebocytes, chondrocytes, osteocytes, osteoblasts, nerve cells and combinations thereof.

16. The support of claim 15, wherein said blood cells are macrophages, lymphocytes, or combinations thereof.

17. The support of claim 1, wherein said porous matrix comprises at least normal, genetically modified or malignant fibroblasts, and wherein said membrane comprises normal, genetically modified or malignant living cells selected from the group consisting of: keratinocytes, melanocytes. Merkel's cells, Langerhans' cells originating from the blood, sebocytes, cells originating from the blood, nerve cells, and combinations thereof.

18. The support of claim 1, wherein said membrane is prepared prior to combination with said porous matrix.

19. The support of claim 18, wherein the collagen membrane is prepared and then laid on a collagen gel before the combination of the collagen sponge and of the collagen membrane is frozen and lyophilized.

20. A support for tissue engineering comprising:
a porous matrix prepared from a collagen gel of aquatic origin; and
a collagen membrane,
wherein said porous matrix is covered on at least one side with said collagen membrane; and
wherein at least one of said porous matrix and of said collagen membrane is produced from a collagen gel containing a mixture of soluble collagen and insoluble collagen.

21. The support of claim 20, wherein said insoluble collagen comprises collagen fibers.

22. The support of claim 1, wherein at least part of the collagen of at least said porous matrix and of said collagen membrane is selected from the group consisting of: type I collagen and type III collagen.

23. The support of claim 1, wherein at least one of said porous matrix and of said collagen membrane is produced from a collagen gel containing a mixture of soluble collagen and insoluble collagen, and wherein at least part of the collagen of at least said porous matrix or said collagen membrane is selected from the group consisting of: type I collagen and type III collagen.

24. The support of claim 1, wherein said compression is performed at a pressure ranging from about 50 bar to about 200 bar.

25. The support of claim 24, wherein said compression is performed at a temperature ranging from about 20° C. to about 80° C.

26. The support of claim 25, wherein said compression is performed at a temperature ranging from about 40° C. to about 60° C.

27. The support of claim 1, wherein said collagen of aquatic origin is derived from the group consisting of: jellyfish, saltwater fish, freshwater fish, and combinations thereof.

28. The support of claim 1, wherein said collagen of aquatic origin is derived from the skin of a flat fish.

29. A biomaterial, selected from the group consisting of: a reconstituted connective tissue comprising a support of claim 1, a reconstituted skin comprising a support of claim 11, a reconstituted corrective tissue comprising a support of claim 20, and a reconstituted skin comprising a support of claim 20.

30. The biomaterial of claim 29, comprising living cells selected from the group consisting of fibroblasts, keratinocytes, melanocytes, Langerhans' cells originating from the blood, endothelial cells originating from the blood, Merkel's cells, blood cells, adipocytes, sebocytes, chondrocytes, osteocytes, nerve cells and osteoblasts.

31. The biomaterial of claim 29, wherein said porous matrix comprises at least normal, genetically modified or malignant fibroblasts, and wherein said membrane comprises normal, genetically modified or malignant living cells selected from the group consisting of: keratinocytes, melanocytes, Merkel's cells, Langerhans' cells oginating from the blood, sebocytes, cells originating from the blood, and nerve cells.

32. An artificial skin comprising a support comprising aquatic collagen, said support comprising a porous matrix prepared from a collagen gel of said aquatic collagen, said porous matrix being covered on at least one side with a collagen membrane comprising a compressed collagen sponge, wherein said compression is carried out at a pressure of at least about 50 bar, and wherein at least one of said porous matrix and of said collagen membrane comprises living cells selected from the group consisting of normal living cells, genetically modified living cells, and malignant living cells.

33. The artificial skin of claim 32, wherein said porous matrix contains normal, genetically modified or malignant fibroblasts, and said collagen membrane comprises living cells selected from the group consisting of: keratinocytes, melanocytes, cells originating from the blood, Merkel's cells, Langerhans' cells originating from the blood, sebocytes and nerve cells.

34. The artificial skin of claim 32, wherein at least one of said porous matrix and of said collagen membrane is produced from a collagen gel containing a mixture of soluble collagen and insoluble collagen.

35. The artificial skin of claim 34, wherein said insoluble collagen comprises collagen fibers.

36. The artificial skin of claim 32, wherein at least part of the collagen of at least said porous matrix and of said membrane is selected from the group consisting of: type I collagen and type III collagen.

37. The artificial skin of claim 32, wherein sad collagen of aquatic origin is obtained from fish skin.

38. The artificial skin of claim 32, wherein said collagen membrane is of aquatic origin.

39. The artificial skin of claim 32, wherein at least one of said porous matrix and of said collagen membrane is produced from a collagen gel containing a mixture of soluble collagen and insoluble collagen, and wherein at least part of the collagen of at least said porous matrix and of said membrane is selected from the group consisting of: type I collagen and type III collagen.

40. A method of reconstructing damaged areas of skin in vivo comprising performing said reconstruction with an artificial skin selected from the group consisting of an artificial skin comprising a support of claim 11, an artificial skin comprising a support of claim 23, and an artificial skin as defined in claim 32.

41. The method of claim 40, wherein said collagen gel of aquatic origin is derived from fish skin.

42. The method of claim 40, wherein said collagen membrane is prepared by compressing a collagen sponge at a pressure ranging from about 50 bar to about 200 bar.

43. The method of claim 40, wherein said collagen membrane is prepared from a compressed collagen sponge compressed at a pressure ranging from about 50 bar to about 200 bar and at a temperate ranging from about 20° C. to about 80° C.

44. The method of claim 40, wherein said collagen membrane comprises collagen derived from fish skin.

45. The method of claim 40, wherein said collagen membrane is derived from fish skin of a flat fish.

46. The method of claim 40, wherein at least one of said collagen of the porous matrix and of the collagen membrane is derived from the group consisting of: jellyfish, saltwater fish, freshwater fish, and combinations thereof.

47. A support for tissue engineering comprising:
a porous matrix prepared from a first collagen gel of aquatic origin and
a collagen membrane comprising a dried collagen film obtained by drying a second collagen gel,
wherein said porous matrix is covered on at least one side with said collagen membrane.

48. The support of claim 47, wherein said first collagen gel of aquatic origin is obtained from fish skin.

49. The support of claim 47, wherein said first collagen gel of aquatic origin is obtained from fish skin in its native form.

50. The support of claim 47, wherein said porous matrix is prepared from said aquatic first collagen gel which has undergone a lyophilization step, and wherein said porous matrix has its mechanical strength or its resistance to enzymatic digestion increased by a physical crosslinking.

51. The support of claim 50, wherein said physical crosslinking comprises thermal dehydration.

52. The support of claim 47, wherein said porous matrix is crosslinked by a chemical method selected from the group consisting of: a treatment with diphenylphosphorylazide, a treatment with a carbodiimide, a treatment with N-hydroxysuccinimide, a treatment with glutaraldehyde, and combinations thereof.

53. The support of claim 47, wherein said first collagen gel of aquatic origin is mixed with chitosan prior to formation of said porous matrix.

54. The support of claim 53, wherein said first collagen gel of aquatic origin is mixed with at least one glycosaminoglycan prior to formation of said porous matrix.

55. The support of claim 54, wherein said glycosaminoglycan is chondroitin sulfate.

56. The support of claim 47, wherein said collagen membrane comprises a collagen film obtained by drying a second collagen gel made from collagen of aquatic origin.

57. The support of claim 47, wherein at least one of said porous matrix and of said collagen membrane comprises living cells selected from the group consisting of normal living cells, genetically modified living cells and malignant living cells.

58. The support of claim 57, wherein said living cells originate from young subjects.

59. The support of claim 57, wherein said living cells originate from elderly subjects.

60. The support of claim 57, wherein said living cells originate from human subjects.

61. The support of claim 57, wherein said living cells are selected from the group consisting of: fibroblasts, keratinocytes, melanocytes, Langerhans' cells originting from the blood, endothelial cells originating from the blood, Merkel's cells, blood cells, adipocytes, sebocytes, chondrocytes, osteocytes, osteoblasts, nerve cells and combinations thereof.

62. The support of claim 61, wherein said blood cells are macrophages, lymphocytes, or combinations thereof.

63. The support of claim 47, wherein said porous matrix comprises normal, genetically modified or malignant fibroblasts, and wherein said collagen membrane comprises normal, genetically modified or malignant living cells selected from the group consisting of: keratinocytes, melanocytes, Merk-el's cells, Langerhans' cells originating from the blood, sebocytes, cells originating from the blood, nerve cells, and combinations thereof.

64. The support of claim 47, wherein said collagen membrane is prepared prior to combination with said porous matrix.

65. The support of claim 64, wherein the collagen membrane is prepared and then laid on a collagen gel before the combination of the collagen membrane and of the collagen gel is frozen and lyophilized.

66. A support for tissue engineering comprising:
a porous matrix prepared from a first collagen gel of aquatic origin; and
a collagen membrane comprising a dried collagen film obtained by drying a second collagen gel,
wherein said porous matrix is covered on at least one side with said collagen membrane; and
wherein at least one of said porous matrix and of said collagen membrane is produced from a collagen gel containing a mixture of soluble collagen and insoluble collagen.

67. The support of claim 66, wherein said insoluble collagen comprises collagen fibers.

68. The support of claim 49, wherein at least part of the collagen of at least said porous matrix and of said collagen membrane is selected from the group consisting of: type I collagen and type III collagen.

69. The support of claim 47, wherein at least one of said porous matrix and of said collagen membrane is produced from a collagen gel containing a mixture of soluble collagen and insoluble collagen, and wherein at least part of the collagen of at least said porous matrix and of said collagen membrane is selected from the group consisting of: type I collagen and type III collagen.

70. The support of claim 47, wherein said collagen of aquatic origin is derived from the group consisting of: jellyfish, saltwater fish, freshwater fish, and combinations thereof.

71. The support of claim 47, wherein said collagen of aquatic origin is derived from the skin of a flat fish.

72. The support of claim 66, wherein said collagen of aquatic origin is derived from the group consisting of: jellyfish, saltwater fish, freshwater fish, and combinations thereof.

73. The support of claim 66, wherein said collagen of aquatic origin is derived from the skin of a flat fish.

74. The support of claim 66, wherein the second collagen gel used to obtain the collagen film by drying is obtained from a collagen of aquatic origin derived from the group consisting of: jellyfish, saltwater fish, freshwater fish, and combinations thereof.

75. A biomaterial, selected from the group consisting of: a reconstituted connective tissue comprising a support of claim 47, a reconstituted skin comprising a support of claim 57, and a reconstituted skin comprising a support of claim 66.

76. The biomaterial of claim 75, comprising living cells selected from the group consisting of: fibroblasts, keratinocytes, melanocytes, Langerhans' cells originating from the blood, endothelial cells originating from the blood, Merkel's cells, blood cells, adipocytes, sebocytes, chondrocytes, osteocytes, nerve cells and osteoblasts.

77. The biomaterial of claim 75, wherein said porous matrix comprises at least normal, genetically modified or malignant fibroblasts, and wherein said membrane comprises normal, genetically modified or malignant living cells selected from the group consisting of: keratinocytes, melanocytes, Merkel's cells, Langerhans' cells originating from the blood, sebocytes, cells originating from the blood, and nerve cells.

78. An artificial skin comprising a support comprising aquatic collagen, said support comprising a porous matrix prepared from a first collagen gel of said aquatic collagen, sad porous matrix being covered on at least one side with a collagen membrane comprising a collagen film obtained by drying a second collagen gel, and wherein at least one of said porous matrix and of said collagen membrane comprises living cells selected from the group consisting of: normal living cells, genetically modified living cells, and malignant living cells.

79. The artificial skin of claim 78, wherein said porous matrix contains at least normal, genetically modified or malignant fibroblasts, and said collagen membrane comprises living cells selected from the group consisting of: keratinocytes, melanocytes, cells originating from the blood, Merkel's cells, Langerhans' cells originating from the blood, sebocytes and nerve cells.

80. An artificial skin comprising a support comprising aquatic collagen, said support comprising a porous matrix prepared from a first collagen gel of said aquatic collagen, said porous matrix being covered on at least one side with a collagen membrane comprising a collagen film obtained by drying a second collagen gel, and wherein at least one of said porous matrix or said collagen membrane comprises living cells selected from the group consisting of: normal living cells, genetically modified living cells, and malignant living cells, and wherein at least one of said porous matrix and of said collagen membrane is produced from a collagen get containing a mixture of soluble collagen and insoluble collagen.

81. The artificial skin of claim 80, wherein said isoluble collagen comprises collagen fibers.

82. The artificial skin of claim 78, wherein at least part of the collagen of at least said porous matrix and of said membrane is selected from the group consisting of: type I collagen and type III collagen.

83. The artificial skin of claim 78, wherein said collagen of aquatic origin is obtained from fish skin.

84. The artificial skin of claim 78, wherein said collagen membrane comprises a collagen film obtained by drying a second collagen gel made from collagen of aquatic origin.

85. The artificial skin of claim 78, wherein at least one of said porous matrix and of said collagen membrane is produced from a collagen gel containing a mixture of soluble collagen and insoluble collagen, and wherein at least part of the collagen of at least said porous matrix and of said membrane is selected from the group consisting of: type I collagen and type III collagen.

86. A method of reconstructing damaged areas of skin in vivo comprising performing said reconstruction with an artificial skin selected from the group consisting of an artificial skin as defined in claim 78, and an artificial skin as defined in claim 80.

87. The method of claim 80, wherein said first collagen gel of aquatic origin is derived from fish skin.

88. The method of claim 80, wherein said collagen membrane comprises a collagen film obtained by drying a second collagen gel of aquatic origin comprising collagen derived from fish skin.

89. The method of claim 86, wherein said collagen of the collagen membrane is derived from the fish skin of a flat fish.

90. The method of claim 86, wherein said collagen of the first collagen gel and of the second collagen gel is derived from the skin of a fish selected from the group consisting of: jellyfish, saltwater fish, freshwater fish, and combinations thereof.

91. The support of claim 47, wherein the collagen film is dried in air.

* * * * *